(12) United States Patent
Poggie et al.

(10) Patent No.: US 8,900,303 B2
(45) Date of Patent: Dec. 2, 2014

(54) POROUS BONE REINFORCEMENTS

(75) Inventors: Matthew P. Poggie, Montclair, NJ (US);
Anthony K. Hedley, Paradise Valley, AZ (US); Nicholas Nai Guang Dong, Little Falls, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 13/544,172

(22) Filed: Jul. 9, 2012

(65) Prior Publication Data
US 2014/0012390 A1    Jan. 9, 2014

(51) Int. Cl.
*A61F 2/28* (2006.01)
*A61F 2/32* (2006.01)
*A61B 17/86* (2006.01)
*A61F 2/34* (2006.01)
*A61B 17/68* (2006.01)
*A61B 17/17* (2006.01)
*A61B 17/84* (2006.01)
*A61F 2/30* (2006.01)

(52) U.S. Cl.
CPC ......... *A61F 2/34* (2013.01); *A61F 2002/30962* (2013.01); *A61B 17/866* (2013.01); *A61F 2002/30736* (2013.01); *A61F 2002/3092* (2013.01); *A61F 2/30734* (2013.01); *A61F 2002/30011* (2013.01); *A61B 17/68* (2013.01); *A61F 2/30749* (2013.01); *A61F 2002/3412* (2013.01); *A61F 2002/30112* (2013.01); *A61F 2002/30433* (2013.01); *A61B 17/1746* (2013.01); *A61B 17/846* (2013.01); *A61F 2002/30205* (2013.01); *A61F 2002/30822* (2013.01)
USPC .................. 623/16.11; 623/11.11; 623/22.11; 623/18.11

(58) Field of Classification Search
CPC ......................................................... A61F 2/28
USPC ................................................. 623/11–23.43
See application file for complete search history.

(56) References Cited

U.S. PATENT DOCUMENTS

| | | | |
|---|---|---|---|
| 2,080,118 A | 5/1937 | Dubbs | |
| 5,310,408 A | 5/1994 | Schryver et al. | |
| 5,314,487 A | 5/1994 | Schryver et al. | |
| 5,314,490 A | 5/1994 | Wagner et al. | |
| 5,360,452 A | 11/1994 | Engelhardt et al. | |
| 5,702,447 A | 12/1997 | Walch et al. | |
| 5,702,477 A | 12/1997 | Capello et al. | |
| 5,785,710 A * | 7/1998 | Michelson | 606/247 |
| 5,871,548 A | 2/1999 | Sanders et al. | |
| 6,162,257 A | 12/2000 | Gustilo et al. | |
| 6,306,173 B1 | 10/2001 | Masini | |
| 6,458,161 B1 | 10/2002 | Gibbs et al. | |

(Continued)

FOREIGN PATENT DOCUMENTS

EP    0499475 A2    8/1992

*Primary Examiner* — Jason-Dennis Stewart
(74) *Attorney, Agent, or Firm* — Lerner, David, Littenberg, Krumholz & Mentlik, LLP

(57) ABSTRACT

A method of reinforcing the bone in an acetabulum for receiving a prosthetic acetabular implant includes preparing a surface of the acetabulum to receive an acetabular implant. At least one porous generally cylindrical bone reinforcement element is provided. At least one bore is drilled in an area of the acetabulum receiving the prosthetic acetabular implant for receiving at least one and preferably more reinforcement elements in the form of cylindrical pilings. The cylindrical porous bone reinforcement element is inserted in the bore such that an exposed surface of the porous bone reinforcement element is adjacent the surface of the acetabulum. The acetabular implant is then implanted with an outer surface of the acetabular implant supported by the reinforcement members.

23 Claims, 10 Drawing Sheets

(56) References Cited

U.S. PATENT DOCUMENTS

| | | |
|---|---|---|
| 7,537,664 B2 | 5/2009 | O'Neill et al. |
| 7,713,306 B2 | 5/2010 | Gibbs |
| 2004/0153082 A1* | 8/2004 | Howie et al. .................... 606/86 |
| 2007/0142914 A1 | 6/2007 | Jones et al. |
| 2010/0094420 A1* | 4/2010 | Grohowski, Jr. ........... 623/16.11 |
| 2011/0035012 A1* | 2/2011 | Linares ....................... 623/18.11 |
| 2012/0095471 A1* | 4/2012 | Linares ........................... 606/80 |
| 2012/0245647 A1* | 9/2012 | Kunz et al. .................. 606/86 R |

* cited by examiner

POROUS BONE REINFORCEMENTS

BACKGROUND OF THE INVENTION

Revision hip surgery poses many challenges for the orthopedic surgeon and is sometimes associated with poorer long term outcomes for the patient than primary surgery. One such challenge is related to the loss of bone that results from the erosion of bone that is caused by a loosened primary implant and/or the process of removing the initial implant.

As is the case for primary surgery, the durability of implant fixation relies on the ability of the host bone to support the prosthesis over the longer term. In revision surgery, the host bone may be compromised and it is incumbent upon the surgeon to recreate a supportive bed for the revision prosthesis. Common techniques that are used to achieve this include bone grafting (autograft and allograft), the use of custom designed prosthesis that intend to fill the space once occupied by host bone and by adding shaped implant augments to a standard implant such as, for example, an acetabular cup.

Each of these techniques have limitations and problems. Autograft bone is in limited supply and often difficult to harvest creating comorbidities for the patient. Allograft bone is expensive and may or may not incorporate with the host and poses the potential for an immune response by the patient. On the other hand, custom prostheses are expensive, inexact, owing to limitations with pre-operative imaging and design. Custom prosthesis replace natural tissue with bulky, stiff implant materials that shield the host bone from stress necessary to maintain bone mineral density for the long term. Augments, like custom prosthesis, may not fit precisely and present additional bulk that can irritate soft tissue and are challenged with having adequate host bone support themselves. Surgical placement of these relatively bulky implants is often complicated and requires extensive undesirable patient exposure.

Implants of this type for the acetabulum are shown in U.S. Pat. Nos. 5,314,490; 5,702,477; 5,871,548; 6,306,173; and 7,713,306. The supplemental support structure shown in U.S. Pat. No. 5,702,447, for example, has segments extending outside the acetabulum for attachment to pelvic bone. Fixation is difficult to achieve and this rather bulky implant invades soft tissue space.

BRIEF SUMMARY OF THE INVENTION

One aspect of the present invention is directed to preparing a support structure for a revision acetabular component in revision total hip surgery using pins or pilings implanted in the pelvis. This concept while discussed in connection with the acetabulum could be applied to other joints, for example, the shoulder (glenoid).

The purpose of the pins or pilings is to provide support for an acetabular shell component (or glenoid component) much like pilings driven deep into a sandy shoreline to provide support for a beach house. For this orthopedic application, the surgeon will identify several locations within the patient's acetabulum to drive the pilings deep into the hemi pelvis. The anterior and posterior columns and the illiac wing present ideal areas to contain the pilings owing to the relative availability of host bone and the line of action of biomechanical forces applied to the hip joint during patient activities. By placing the pilings in this manner, the surgeon can reconstruct the acetabulum from within by placing implant components within the volume that the natural bone occupies rather than placing implant components on bone surfaces that are outside of this envelope for example, the acetabulum. This avoids the related problems of improper fit and fixation and the bulky prosthetic components complicating exposure and irritating surrounding soft tissue.

The surgical exposure required to prepare for and place the pilings is similar to that required for other primary implant procedures, e.g., acetabular shell adjuvant screw fixation. Placement of the pilings is done by the surgeon during implantation, preferably in the drilled/reamed acetabular cavity for the desired press-fit of an acetabular prosthetic implant. Once the site is prepared, the pilings can be simply placed and impacted with a driver instrument. Pilot holes can be drilled to accommodate the pilings. It is preferred that the pilings make intimate contact with the acetabular implant that is placed opposite the pilings. This can be facilitated through the use of a tamp that matches the outer diameter of the acetabular shell which may be part-spherical in shape. By using this tool, multiple pilings can be driven to their final position simultaneously. The acetabular bed can be further augmented with a layer of bone graft that fills the space between pilings that are deliberately left in a slightly proud or protruded position relative to the floor of the acetabulum. Here, the aforementioned insertion tamp can be used to simultaneously impact the graft and drive the pilings to the preferred position.

Location of and preparation for the pilings can be enhanced through the use of patient-specific instrumentation that is designed and fabricated based off of pre-operative imaging, such as a CAT scan, MRI or X-ray in a similar manner that is used to prepare for and place osseous implants for dental procedures.

The pilings can be at least partially porous and can be fabricated through a variety of means. One such method is the additive layer by layer laser technique disclosed in U.S. Pat. No. 7,537,664 and U.S. Patent Publication No. 2007/0142914, the disclosures of which are incorporated herein by reference. These methods can be used to provide pilings made of, for example, titanium alloy having varying porosity with a denser or solid center. The piling design would present a highly porous surface region intended to directly oppose host bone and to allow bone ingrowth for long term fixation. The pilings would be offered in various shapes, diameters and lengths to accommodate placement in various regions of the acetabulum and to account for various degrees of bone loss. In addition the pilings can have various surface textures to enhance initial fixation and/or osseous integration, e.g., roughened, acid etched, threaded, barbed, grooved, etc. The pilings could be fully porous or porous only on the outer surface in an effort to strengthen the overall component. An internal thread can be incorporated in the piling to accommodate a screw that is placed through the acetabular shell to anchor the piling to the shell and/or host bone.

Many variants of the piling design and placement can be envisioned. The piling can be cylindrical or conical or a combination of the two or even polygonal. What is disclosed is a simple means to provide solid, long lasting support for an acetabular implant component for use in complex revision procedures. The proposed design avoids many difficulties encountered with current implant components.

The pilings can be used in a method for reinforcing a bone structure such as an acetabulum. A plurality of reinforcement members such as the piling described herein can be obtained each having a non-uniform surface. A plurality of spaced recesses is formed in a surface of a bone structure, such as the acetabulum, for receiving the plurality of reinforcement members such as pilings. The plurality of reinforcement members are inserted into the recesses formed in the bone structure so that an exposed surface of each of the reinforcement members is at or above the bone structure surface. A prosthetic joint component is then implanted in contact with the exposed surface of the reinforcement members. The reinforcement members are cylindrically shaped and comprise porous metal. The spaced recesses may be cylindrical bores or may be conical recesses or a conical recess with a cylindrical end bore portion in the bone and extend along an axis preferably generally perpendicular to a bone surface adjacent the cylindrical bores. The bores are drilled using a template. The bone structure may be an acetabulum with the template having a part-spherical shape and the bores are drilled using a drill guide. The cylindrically or conically shaped reinforcement members may have solid metal cores having a porous outer surface.

An additional method of reinforcing the bone in an acetabulum for receiving a prosthetic acetabular implant includes preparing a surface of the acetabulum to receive an acetabular implant. At least one porous bone reinforcement element is obtained. At least one bore is drilled in an area of the acetabulum receiving the prosthetic acetabular implant. The porous bone reinforcement element is inserted in the bore such that an exposed surface of the porous bone reinforcement element is adjacent the surface of the acetabulum. The acetabular implant is thereafter implanted with an outer surface of the acetabular implant supported by the reinforcement element or elements. The reinforcement elements may be cylindrical or conical in shape and comprise porous metal. The bores or recesses in the bone preferably extend along an axis generally perpendicular to a bone surface adjacent the recesses or bores. The bores may be drilled using a template. The bone structure may be an acetabulum with the template having a part-spherical shape. The cylindrical bores are drilled using the template and a drill guide. The cylindrically or conically shaped reinforcement members preferably have solid metal cores having a porous outer surface however the reinforcement members could be all porous.

This simplest piling or reinforcement member lends structural integrity to the acetabular bone bed that has been comprised by prior surgery and/or osteolysis from a failed previous implant. Porous cylindrical pilings are placed in regions of the acetabulum that show evidence of compromised bone structure. The porous biocompatible material will induce new bone formation and the relatively strong stiff implant, once ingrown, will provide structural integrity to the acetabular bone bed better enabling it to support an implanted acetabular component. The porous cylindrical pilings can be placed flush with the reamed acetabular bed to act as a reinforcing bar for the bone or they can protrude from the acetabular bed through a defect void and make direct contact with the implanted acetabular component. One or more pilings can be placed within the acetabulum and against the acetabular shell according to the situation that presents. Another form of the simple cylindrical piling includes an extension with a surface that forms part of a sphere. The spherical extension fans out from a cylindrical piling to provide for greater surface area coverage and support for the acetabular implant component. The spherical radius dimension corresponds to acetabular implant dimension OD sizing typically in the range of 50 to 80 mm.

Alternately, conical pilings with abutments are a two piece assembly comprising a piling element and an abutment element. The piling element has a cylindrical proximal projection extending from a conical distal portion. The conical element provides a tapered hole into which the tapered projection of the abutment component can mate. The abutment has a tapered projection for engaging the tapered hole within the piling component. The body of the abutment is provided in various shapes and sizes that intend to fill a void space between the acetabular bone and an implanted acetabular shell. The abutment is positioned to directly contact and support the acetabular shell while connecting, via the locking taper, to the impacted piling component. One or more assemblies of the piling/abutment configuration can be placed within the acetabulum and against the acetabular shell according to the situation that presents. Another variant is described where two or more of the abutments are configured and placed in a way similar to that described above. Rather than the abutments providing direct support for an acetabular shell component they are positioned to create a cavity, for example 2 mms into which bone cement is placed and a polyethylene bearing component is affixed.

A wide array of piling sizes are offered to fit the varying pelvic sizing and placement locations. A Virtual Bone Database can be utilized to develop the array of sizes. The pilings are configured in simple shapes (cylinders, cones) to facilitate powered reaming preparation. Diametrical increments of 2 mm are offered to provide for a precise fit. Diameters and lengths are offered to accommodate placement within the bony vault. All external surfaces are porous with a three dimensional scaffold structure suitable for bone in-growth. There is an internal solid core for load carrying capacity and the provision for a tapered cavity. In the acetabulum the primary region of engagement for the piling component is within the posterior column. The bone near the sciatic notch is generally of dense, strong quality and is a primary engagement point. From there a cylindrical portion extends proximally. Distally to the acetabular bed the piling tapers to a larger diameter. The secondary engagement region is within the anterior column. This region will accommodate smaller sized components as compared with the posterior column. The distal end of the piling component houses a common tapered hole that accepts the common tapered projection of the abutment component. The abutment component has a common tapered projection for engagement with the tapered hole of the piling component. The abutment body is provided in varied sizes. The purpose of the abutment is to bridge the gap between the embedded piling element and an acetabular component that is positioned anatomically within the prepared acetabular bed. Owing to the variability that presents in revision surgery a multitude of sizes may be offered. The surface of the abutment that engages the acetabular shell is shaped in the form of a spherical radius to mimic the shape of the acetabular components that it will engage. Sizes used routinely for revision surgery range from 50 to 80 mm. Cylindrical pilings are offered in an array of diameter and length combinations.

The surgical technique for implanting a conical piling and abutment include providing adequate exposure to gain a straight line access to the posterior column. A trochanteric osteotomy will facilitate this. A bed for the acetabular shell component is prepared by sequentially reaming up in size to span the dimension between the anterior and posterior columns. The sciatic notch is referenced to position a guide wire insertion tool or jig. A hole is drilled for the guide wires through a positioned jig. Image intensification is used to ascertain position of guide wire in all planes. The guide wire penetration depth is measured to select the appropriate piling length. Recesses are sequentially prepared for the piling with a guided tapered reamer to establish the definitive size based on resistance to preparation from surrounding cortico-cancellous bone. To facilitate drilling and reaming, sequential preparation with shortened cutters, placed over the guide wire, can be utilized. The appropriate piling configuration is chosen based on line-to-line reamer preparation. The pilings are placed in the prepared site and impacted with a bullet tipped driver until fully seated. An acetabular shell trial is positioned to assess defect size by placing trials in order to select the appropriate size of the abutment. The shell trial is then removed. The tapered post of the chosen abutment is placed within the tapered hole for the piling and impacted to engage the taper lock. Bone graft is packed in any void between piling and abutment. The acetabular shell is impacted to fit within reamed AP columns and against piling abutments. Bone cement or other formable material can be packed or injected in any void space between acetabular shell and abutment.

In revision situations a failed implant that may be situ or a pre-existing anatomic deformity could benefit from the piling implant. Initially a surgeon obtains a pre-op CT image of acetabulum. A shape matched jig is prepared for preferentially locating the guide wire positioning for the pilings that are to be used. The piling size is determined from the 3D image. A jig is placed in the acetabular bed (after removal of the existing implant). The sciatic notch can be used as one jig location reference. At least two other positioning reference points can be identified in the pre-op plan based on the anatomy that presents. The jig is sized to facilitate insertion of the flexible drill drive shaft. A low profile configuration is preferred. A hole for the guide wires through the positioned jig which may be a shape match jig. The jig is then removed and the remaining procedure is the same as that described above.

If a cylindrical piling is used a surgical technique would include providing adequate exposure to gain a straight line access to the posterior column. A trochanteric osteotomy will facilitate this. The bed is prepared for the acetabular shell component by sequentially reaming up in size to span the dimension between the anterior and posterior columns. An acetabular shell trial is used to ascertain fit of the chosen implant size and to target and mark positions for placement of pilings. The length is measured such that the piling will protrude from the bone to contact the outer surface of the acetabular trial. The shell trial is removed. The sciatic notch is referenced to position the guide wire drill guide tool. A hole is drilled for the guide wire through the positioned jig. Image intensification is used to ascertain position of guide wire in all planes. The guide wire penetration depth is measured to select the appropriate length of piling that will be embedded in the bone. Added to that is the length of the piling that will protrude from the bone to contact the acetabular component (if that function is desired). These two measures together will guide the selection of the appropriate length piling. The acetabular is sequentially prepared for the piling with a guided reamer to establish the definitive size based on resistance to preparation from surrounding cortico-cancellous bone. To facilitate reaming, sequential preparation with shortened cutters, placed over the guide wire, can be utilized. The appropriate piling outer diameter is chosen based on line-to-line reamer preparation.

It may be desired to have the pylons make intimate contact with the acetabular shell implant. This is facilitated through the use of a tamp that matches the outer diameter of the chosen acetabular shell. The pilings are placed in the prepared site and impacted with the appropriate tamp until fully seated. Multiple pilings can be impacted simultaneously with the use of the tamp. The acetabular shell is then impacted to fit within reamed AP columns and against pilings.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

DETAILED DESCRIPTION

Figure 1:
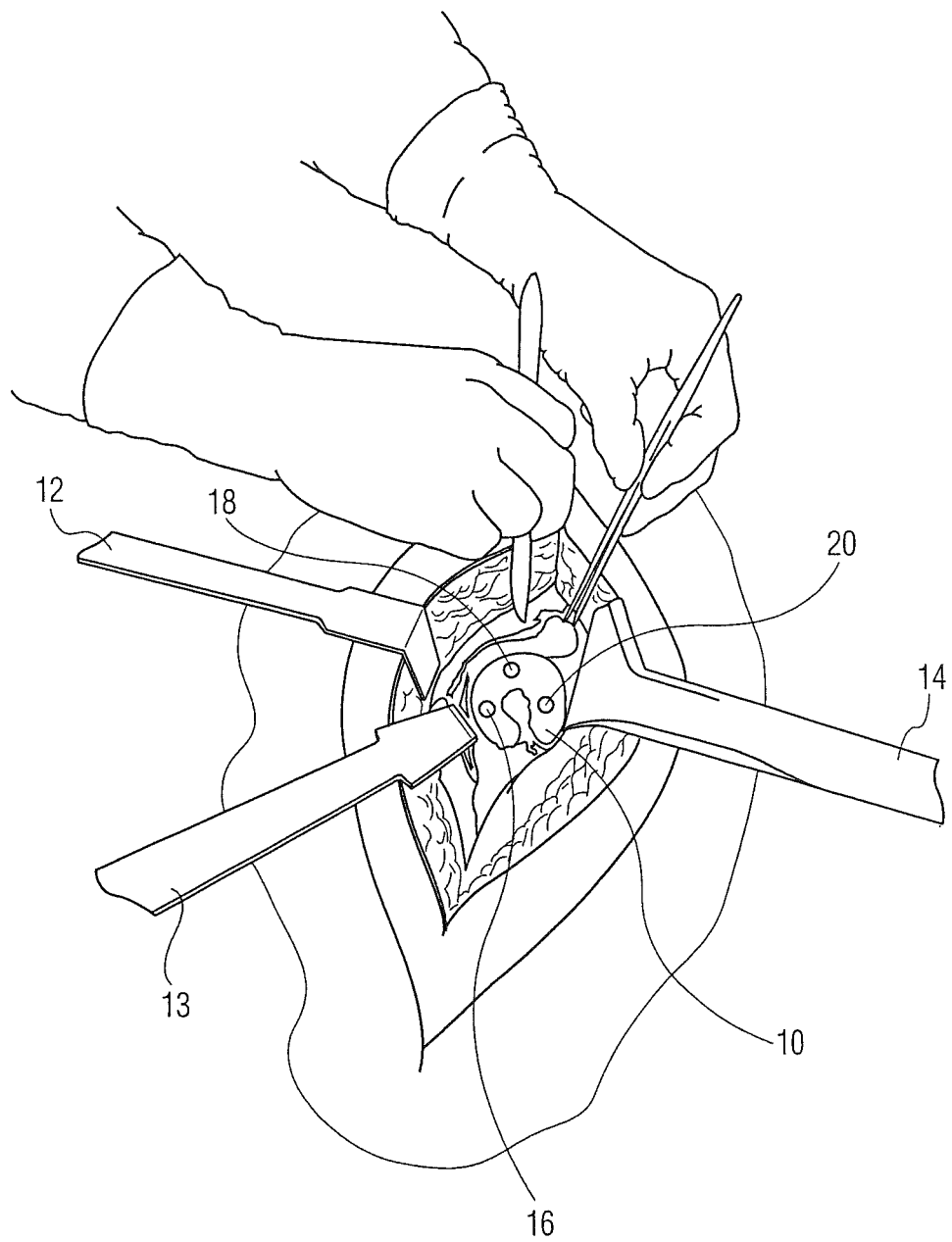
FIG. 1 is a view of the exposed acetabulum indicating three locations for the reinforcement pilings of the present invention.

Referring to FIG. 1 there is shown a surgeon exposing an acetabulum 10 for preparing the acetabulum to receive a typical acetabular implant (not shown). After making an incision retractors 12, 13, and 14 are utilized to keep the incision open while the surgeon prepares the acetabulum. Also indicated in FIG. 1 are three locations 16, 18 and 20 for placing the reinforcement pilings or pins of the present invention.

Figure 2:
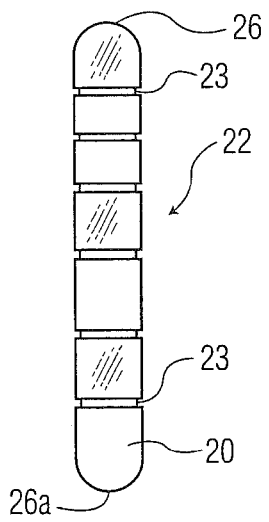
FIG. 2 is a first embodiment of a piling of the present invention.
Figure 3:
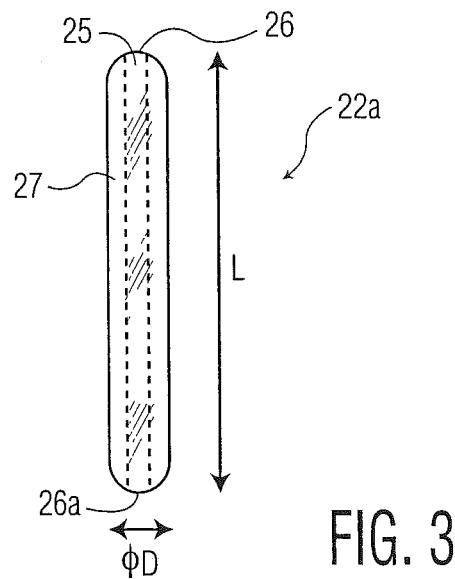
FIG. 3 is a second embodiment of a reinforcement piling of the present invention.
Figure 4:
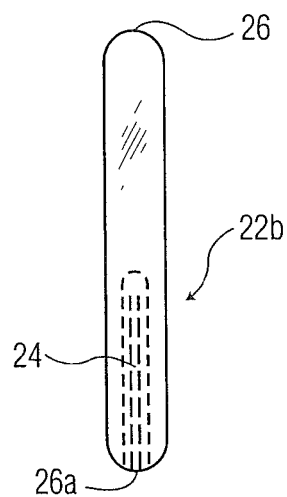
FIG. 4 is yet another embodiment of the reinforcement piling of the present invention.

Referring to FIGS. 2-4 there is shown three embodiments of the reinforcement pilings or pins of the present invention generally denoted as 22, 22a and 22b respectively. Referring to FIG. 2 there is shown a piling or pin 22 made of solid metal such as titanium, stainless steel or cobalt chrome alloy for insertion into the acetabulum. The pin has a cylindrical shape with a diameter of 10 to 30 mm and a length of between 25 and 125 mm. The pin may have a series of spaced circumferential grooves 23 to provide for greater retention of the pin or piling 22 in the bone of the acetabulum 10. Pin 22, or any of the pins, can be coated with a bone growth inducing material such as calcium phosphate. To enhance fixation the grooves have a depth of between 0.25 and 1.0 millimeters. A leading surface 26 may have a convex part-spherical shape or may be pointed for easier insertion into the bone. An end surface or tip 26a of the pin 22 on implantation is located at or slightly above the surface of the prepared acetabulum. End surface 26a may be planar or convex or may be concave in the shape to match the outer surface of the acetabular cup shell outer bone contacting surface.

Referring to FIG. 3 there is shown reinforcement piling or pin 22a which has a solid metal core 25 but has a porous tissue ingrowth surface 27 formed at least partially or completely around the outer surface of the pin or piling 22a. This porous surface may be applied in any well known manner and preferably according to the delective laser melting also known as Laser Rapid Manufacturing process disclosed in U.S. Pat. No. 7,537,664. Of course, pin or piling 22a may be made entirely of porous metal either with a constant porosity or with a porosity that increases on moving from the center of the pin or piling to an outer surface thereof. The pin 22a is made from biocompatible metal as with pin 22. The pin has a diameter D and a length L similar to pin 22. The pore size is in the range of 10 to 1000 microns, preferably between 100 and 400 microns, and the porosity is between 40 and 80%.

Referring to FIG. 4 there is a third embodiment in the form of pin or piling 22b which is similar to that shown in FIG. 2 and d with the exception that it has a threaded counter bore 24 at end 26 thereof which, when pin or piling 22b is implanted in the acetabulum, is adjacent the surface of the acetabulum. The threaded counter bore 24 is designed to receive a screw extending through a bone on the wall of a metal acetabular prosthetic shell (not shown) extending from an inner surface to the bone contacting surface. The shell typically receives a polyethylene bearing element. Thus, when bore 24 receives a screw through the wall of the shell member this couples the pin 22b to the shell and helps prevent rotational movement of the shell within the acetabulum.

While three pins or piling designs 22, 22a and 22b are shown, numerous other variations may be utilized. In addition, while FIG. 1 suggests that three pins or pilings are utilized, more or fewer may also be used depending on the condition of the bone in the pelvis of an individual patient.

Figure 5:
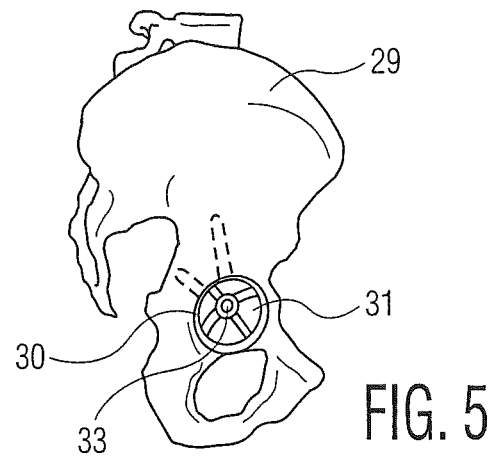
FIG. 5 a view of the acetabulum with a drill guide or template mounted therein.
Figure 6:
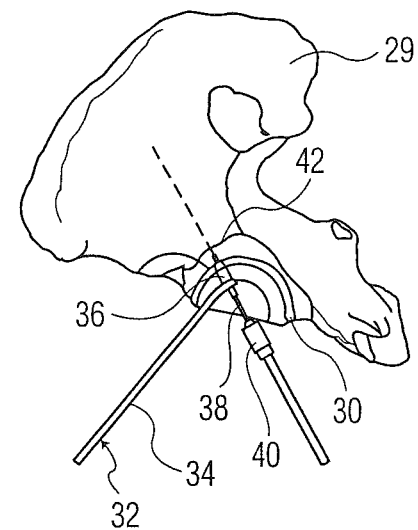
FIG. 6 shows a cross-section of the acetabulum with a drill guide for directing a drill through the template of FIG. 5 for forming pilot holes in the acetabulum.

Referring to FIG. 5 there is shown a pelvis 29 including windowed trial 30 mounted in acetabulum 10 and capable of directing a drill through a central hole 33 for forming a bore for receiving one or multiple pins or pilings as shown in FIGS. 2-4 into the acetabulum. This template can be designed so as to accommodate a drill to guide holes in areas of the pelvis 29 with sufficient bone. The drill guide holes could be on a template (not shown) placed in windows 31 of windowed trial 30. This design can be based on an actual model of the patient's acetabular area produced from data gathered by a series of slices made during a computer aided tomography (CAT) scan or other imaging done prior to the surgical procedure. As shown in FIG. 6 a drill guide 32 having handle 34 and a tubular guide member 36 can be aligned with the locations marked in the template 30 so that a drill bit 38 can be utilized to drill a pilot hole in the pelvis for receiving pilings 22-22b.

Preferably the reinforcement pilings or pins 22-22b preferably have a diameter between 10 mm to 30 mm and a length of between 25 mm to 125 mm and thus drill bit 38 is used having a diameter commensurate with the diameter of the reinforcement pilings or pins and the drill may include a stop element 40 for ensuring that the proper depth of a pilot hole 42 is achieved. Any power device can be used to drive the drill bit 38.

Figure 7:
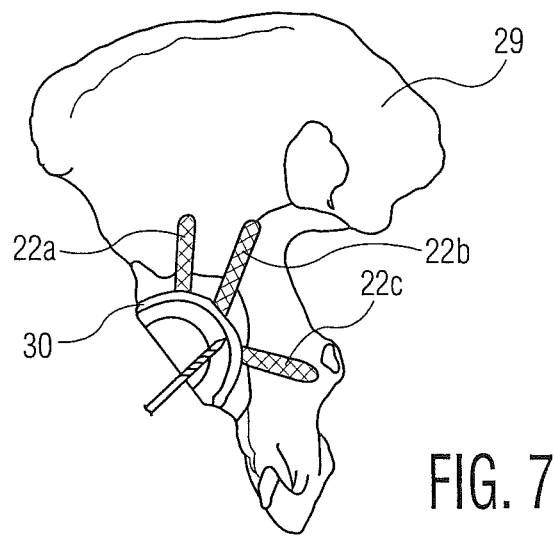
FIG. 7 is a view of the acetabulum of FIG. 6 showing three pilings implanted in the acetabular area of the pelvis.

Referring to FIG. 7 there is shown pins or piling 22a-22c as shown in FIGS. 2-4 implanted in the pilot holes 42. These pins are preferably implanted using a tool such as a part spherically shaped tamp. Pin 22a is directed towards the anterior column (ilium), 22b is directed to the sciatic notch and 22c is directed towards the posterior column (ischium). The order of insertion is 22b first then 22a and if needed 22c. As discussed above, the ends 26 of pins 22-22b preferably stand flush with or stand slightly proud of the prepared surface of the acetabulum. Bone graft can be impacted around the ends 26 of the reinforcement pins or pilings which stand proud of the prepared acetabular surface so that a relatively smooth part-spherical surface is formed within the acetabulum for contacting an outer bone contacting surface of the prosthetic acetabular cup shell member.

Figure 8:
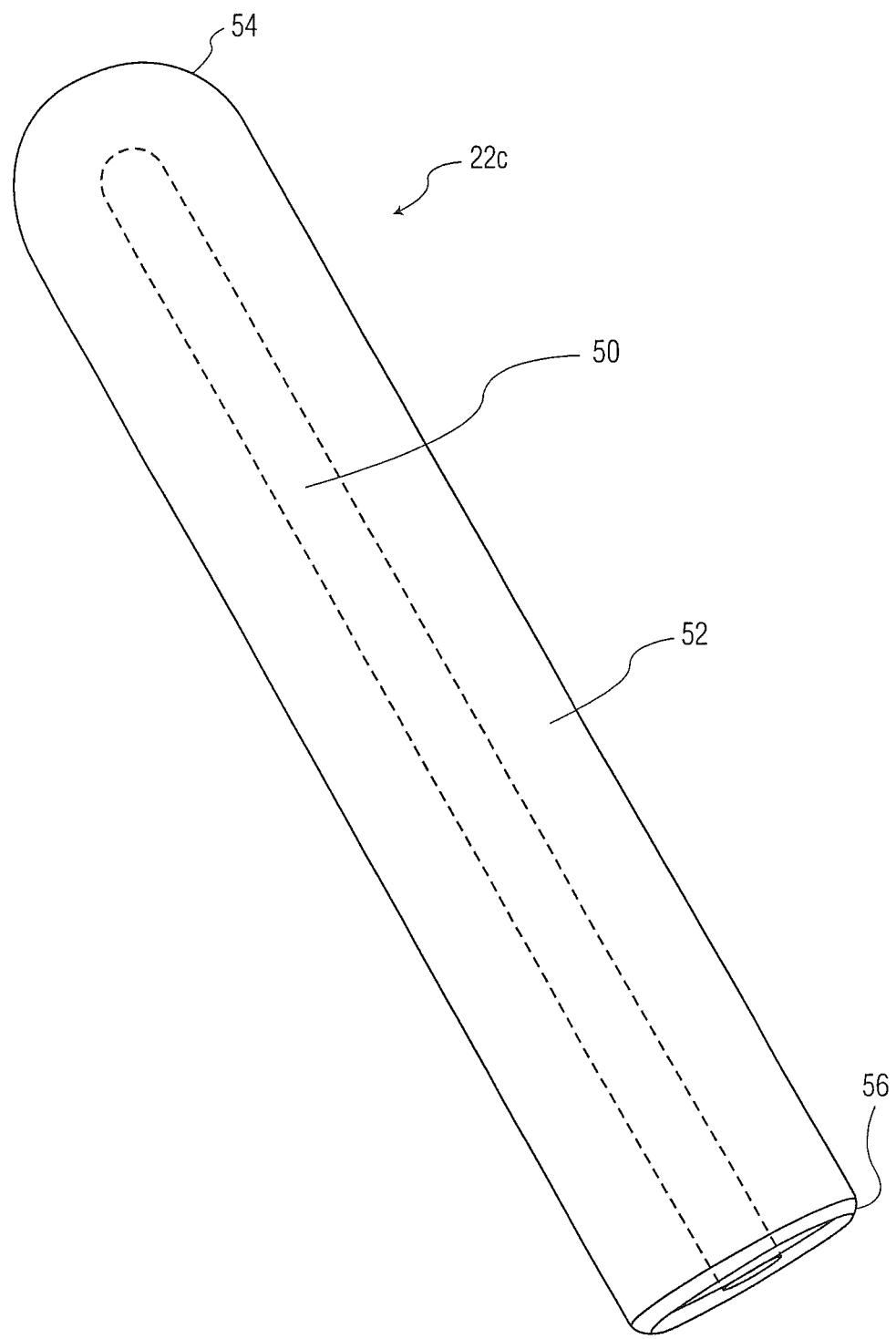
FIG. 8 is an isometric view of an alternate reinforcement piling comprising a solid core shown in phantom surrounded by a porous bone ingrowth structure.
Figure 9:
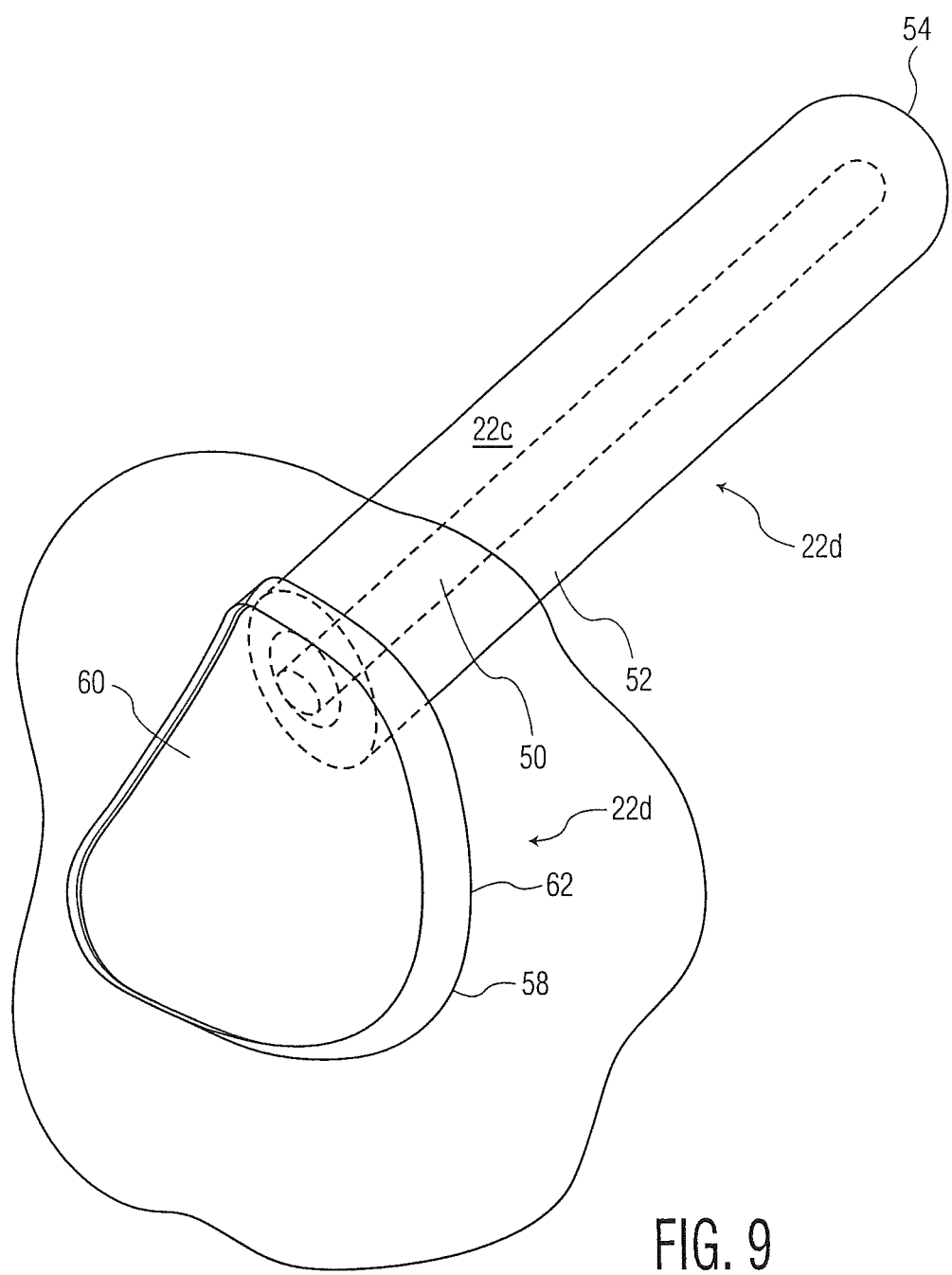
FIG. 9 is an additional alternate reinforcement piling including the structure of FIG. 8 but including an integral flange or abutment formed at one end of the reinforcement piling and shaped to match an acetabular bone surface in which the cylindrical portion of the reinforcement piling is implanted.

Referring to FIG. 8 there is shown an enlarged perspective view of an alternate reinforcement piling generally denote as 22c with a solid core 50 shown in phantom surrounded by a porous structure 52. As shown, both core 50 and porous structure 52 are generally cylindrical. Reinforcement piling 22c includes a part-spherical first or leading end 54 similar to end and a generally planar second end 56. Referring to FIG. 9 there is shown yet an additional alternate embodiment generally denoted as 22d which includes generally cylindrical reinforcement piling 22c including a part-spherical flange member 58 attached to end 56 thereof. Embodiment 22d is formed in its entirety by a single selective laser melting step as described above. Generally this involves first constructing flange 58 by an additive laser melting technique and then building cylindrical reinforcement piling 22c on a surface of flange 58.

As depicted in FIG. 9, part-spherical flange or abutment plate 58 is shaped in a part-spherical manner to contact a surface of the acetabulum and to contact an outer surface of an acetabular cup implanted therein. Thus, flange 58 includes surface 60 designed to receive an outer surface of an acetabular cup implant and surface 62 shaped to contact the prepared surface of the acetabulum. Thus when reinforcement piling 22c is inserted as described above with respect to embodiments 22, 22a and 22b, flange 58 is rotated into a position that matches the contour of the prepared acetabulum. Flange 58 may be either entirely solid or entirely porous or may have a solid part-spherical plate-like core having a porous surface at least on the bone contacting side 62. The flange 58 and piling 22c may be made together by rapid laser manufacturing in a single step process. Reinforcement pilings 22-22c have a part-spherical tip 54 to allow easy insertion into the bore formed in the acetabulum. Of course tip 54 may be pointed.

The piling 22c with the part-spherical end plate may be difficult to precisely fit against the outer diameter of the acetabular shell owing to variable location and orientation of the individual components. A swivel mechanism could be employed to allow adjustment of the piling and the part-spherical end plate. Bone cement could be used to connect the shell to the piling end plate. Multiple pilings with part-spherical endplates could be positioned within the prepared acetabulum and an all polyethylene acetabular insert could be cemented within the contained volume. Mesh could be used to contain graft material placed between the part-spherical end plate at the opening of the acetabulum.

Figure 9A:
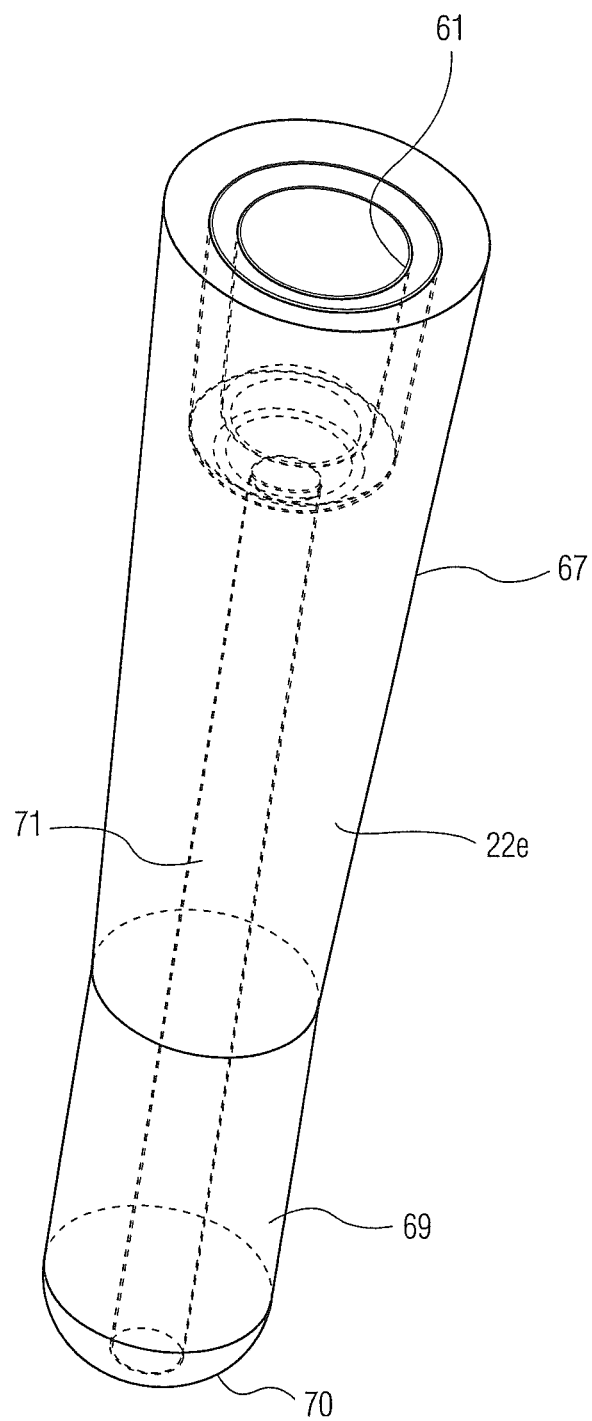
FIGS. 9a-9c show an alternate piling having a modular abutment element attached to the piling by mating male and female tapers.
Figure 9B:
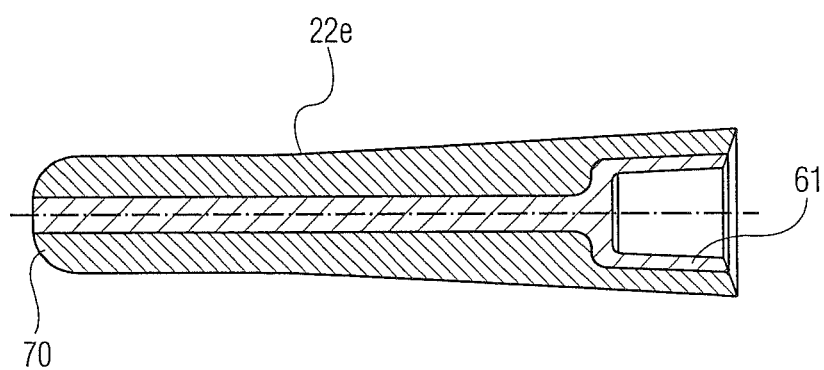
Figure 9C:
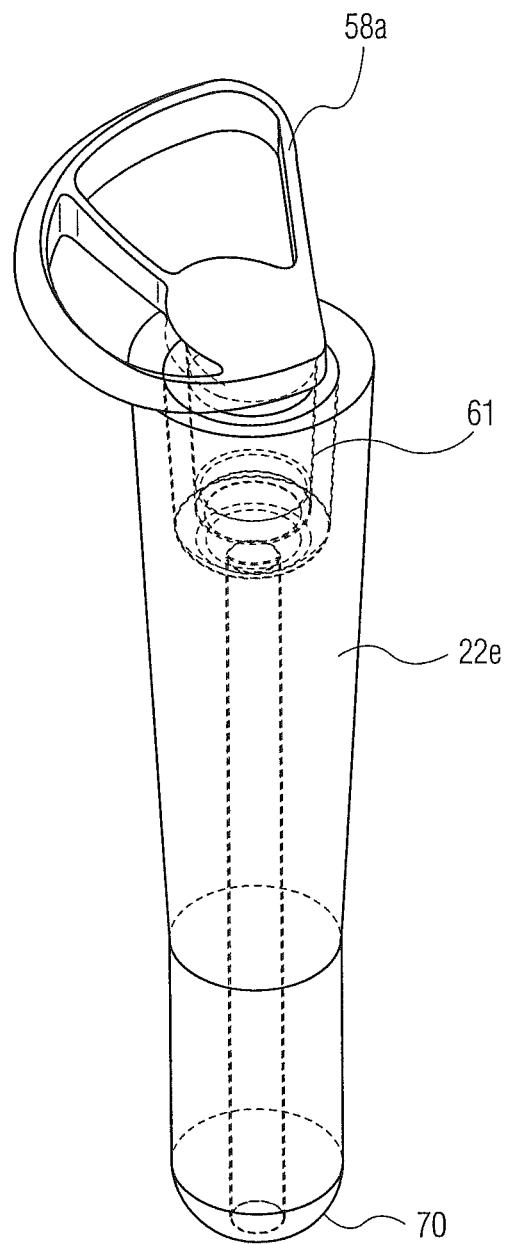

Referring to FIGS. 9a-9c, there is an alternate embodiment of the piling in abutment plate 58 designated in FIGS. 9a-9c as 58a, which has a similar shape to abutment flange 58 with the exception that it has a tapered male connector 59 extending from the bone contacting surface of abutment 58a. Taper connector 59 may be a morse taper and engages a mating conical recess 61 in piling 22e. As shown in FIGS. 9a-9c, piling 22e has a part conical section 67 and a cylindrical section 69 extending from section 67 toward a tip 70 as shown piling 22e also has a cannulated bore extending from the female recess through tip 70. Cannulated bore 71 is sized to receive a typical guide wire used to guide implants into bores formed in bone. While a piling 22e is shown in FIGS. 9a-9c, any style piling could be utilized as long as it includes the tapered socket 61 for attachment to the male tapered extension of flange or abutment element 58*a*. With this design, the piling 22 can be implanted and then a plurality of different sized abutment flanges 58*a* could be provided and attached to the piling at the time of surgery.

Figure 10:
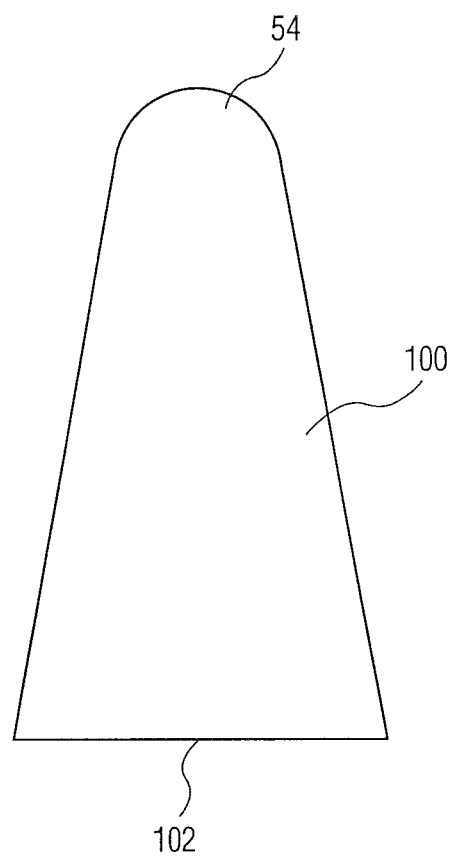
FIGS. 10-11c are alternate piling designs with various shapes.

Alternately, as shown in FIG. 10 a piling 100 may be cone-shaped with a part-spherical tip 54 being the frustum of the cone designed for entry into a conical bore in the acetabulum. The opposite end of the piling 100 has the largest diameter 102 and seats flush or just above (about 2 mm) the prepared surface of the acetabulum. The largest diameter can be concave to match the convex shape of the acetabular implant outer shell. Conical pilings 100 can be impacted to an end point position with the taper preventing migration and can cause less stress shielding as well as providing a broader area of contact with the acetabular shell.

Figure 11A:
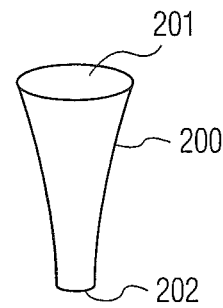
Figure 11B:
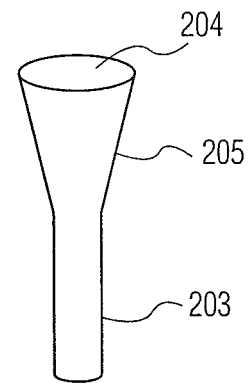
Figure 11C:
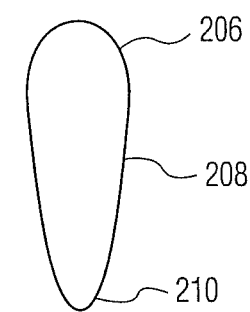

Referring to FIGS. 11A-11C there is shown additional alternate piling designs designated as 200, 205, and 208. Referring to FIG. 11A a conically shaped piling is shown having a concave end surface 201 and a convex opposite end surface 202 which is adapted to be placed in a bore in the acetabulum. Again, concave end surface 201 is designed to match the shape of the outer surface of an acetabular implant outer shell. Referring to FIG. 11B there is shown a hybrid piling having a conical surface 205 followed by a cylindrical portion 203. Again, the surface of the conical portion 205 has a concave surface for contacting the outer acetabular shell. The length of cylindrical portion 203 can vary and thus a kit of pilings of different lengths cylindrical portions 203 can be supplied. Referring to FIG. 11C there is shown an implant with a conical surface 208 having a convex surface of revolution 206, 210 at each end. The convex surface 210 is inserted into a bore drilled in the acetabulum when installing the piling. As alluded to above, all of the pilings disclosed in this application may be supplied as a kit comprising the different shaped pilings, different length pilings and different diameter of pilings such that the surgeon can choose the appropriate implant for each patient.

Drilling for location and orientation of the pilings may be done through a drill guide template to form a pilot hole. A guide wire is then placed in the pilot hole and the hole expanded with a larger diameter drill or a tapered reamer. The drill guide template may be designed to be located initially by using the sciatic notch as a reliable anatomic reference. Extensile exposure is required to gain a straight shot to the posterior column. A trochanteric osteotomy also may be required for access. The bed for the acetabular shell is prepared by reaming up to span the dimension between the anterior and posterior columns. A guide wire insertion tool references the sciatic notch to position a guide wire. A hole is drilled for the guide wire(s) through the positioned template or jig. An image intensifier/c-arm is used to ascertain the position of guide wire in all planes. The guide wire penetration depth is measured to select piling length. The acetabulum is sequentially prepared for the piling with a guided tapered reamer to establish definitive size for an implant based on resistance to preparation from surrounding cortico-cancellous bone. 2 mm diametrical increments are sufficient for reaming and implant sizing. To facilitate drilling and reaming a fractional insertion technique using a flexible shaft can be utilized. A piling configuration is chosen based on line-to-line reamer preparation. Appropriate pilings are placed in the prepared site and impacted with a bullet tipped driver until fully seated. An acetabular shell trial is then positioned and any defect size is assessed by placing trials in order to select the appropriate size of a defect abutment to be assembled at or to a piling. The shell trial is removed. Assemble appropriate abutment to the piling. (See FIGS. 9-9*c*.) Bone-Graft is packed in any void between piling and abutment. The acetabular shell is impacted to fit within the reamed area and against the piling and/or abutment(s). Bone cement or other formable material may be used to fill in any void space between acetabular shell and abutment.

In revision situations a failed implant may be in situ or a pre-existing anatomic deformity could benefit from the piling implant. A pre-op CT image of acetabulum is obtained. A shape match jig for preferentially locating the guide wire positioning for the piling(s) that are to be used is custom designed. The piling size is determined from the 3D image. The jig or template is placed in the acetabular bed (after removal of the existing implant). The sciatic notch can again be used as one jig location reference. At least two other positioning reference points can be identified in the pre-op plan based on the patient's anatomy. The jig or template is sized to facilitate insertion of the flexible drill drive shaft. A low profile configuration is preferred. A hole is drilled for the guide wire(s) through the positioned shape matched jig and the jig is removed. The remainder of the technique is as described above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for reinforcing a prepared bone structure comprising:
    obtaining a plurality of individual reinforcement members each having a porous bone contacting surface and an at least partially solid end surface and obtaining a single individual prosthetic joint component having a bone contacting surface;
    forming a plurality of spaced recesses in a surface of a prepared bone structure for receiving the plurality of reinforcement members, the recesses spaced to leave bone structure surrounding each of the recesses;
    implanting one of the plurality of reinforcement members in each of the plurality of spaced recesses formed in the bone structure so that the end surface of the reinforcement member is at the bone structure surface; and
    implanting the single individual prosthetic joint component with the bone contacting surface in contact with the end surface of each of the reinforcement members and in contact with the bone surface surrounding each individual reinforcement member.

2. The method as set forth in claim 1 wherein the reinforcement members have a cylindrical portion with the exposed surface in the form of a flange having a part-spherical shape extending from an end of the cylindrical portion.

3. The method as set forth in claim 2 wherein the cylindrical portion is porous metal surrounding a solid core.

4. The method as set forth in claim 1, wherein the reinforcement members are cylindrically shaped pilings and comprise porous metal.

5. The method as set forth in claim 4, wherein the spaced recesses are cylindrical bores in the bone.

6. The method as set forth in claim 5, wherein the cylindrical bores extend along an axis generally perpendicular to a bone surface adjacent the cylindrical bores.

7. The method as set forth in claim 6, further comprising drilling the cylindrical bores using a template.

8. The method as set forth in claim 7, wherein the bone structure is an acetabulum and the template has a part-spherical shape.

9. The method as set forth in claim 6, further comprising drilling the cylindrical bores using a drill guide.

10. The method as set forth in claim 4, wherein the cylindrically shaped reinforcement members have solid metal cores having a porous outer surface.

11. The method as set forth in claim 1, wherein the bone structure is an acetabulum.

12. The method as set forth in claim 11 wherein the implantation of the plurality of reinforcement member is done simultaneously by a part-spherically shaped tamp.

13. The method as set forth in claim 1, wherein the reinforcement members are cylindrical and have solid metal cores having a porous outer surface.

14. A method of reinforcing the bone in an acetabulum for receiving a prosthetic acetabular implant having a metal outer shell comprising:
 preparing a surface of the acetabulum to receive an acetabular implant having a metal shell with an outer bone contacting surface;
 obtaining a plurality of individual at least partially porous bone reinforcement elements;
 drilling a plurality of bores in an area of the acetabulum receiving the prosthetic acetabular implant each of the bores surrounded by acetabular bone;
 inserting one of the plurality of individual porous bone reinforcement elements in each of the plurality of bores such that an exposed end surface of each porous bone reinforcement element is adjacent the surface of the acetabulum; and
 implanting the acetabular implant with the outer bone contacting surface of the acetabular implant metal outer shell supported by each of the plurality of inserted reinforcement elements and contacting the acetabular bone surrounding each of the bores in the acetabulum receiving each of the plurality of bone reinforcement elements.

15. The method as set forth in claim 14 wherein the porous end reinforcement elements have a cylindrical portion with the exposed surface in the form of a flange having a part-spherical shape extending from an end of the cylindrical portion.

16. The method as set forth in claim 15 wherein the cylindrical portion is porous metal surrounding a solid core.

17. The method as set forth in claim 14, wherein the reinforcement elements are cylindrically shaped and comprise porous metal.

18. The method as set forth in claim 14, wherein the bore are cylindrical bores which extend along an axis generally perpendicular to a bone surface adjacent the cylindrical bores.

19. The method as set forth in claim 18, further comprising drilling the cylindrical bores using a template.

20. The method as set forth in claim 19, wherein the bone structure is an acetabulum and the template has a part-spherical shape.

21. The method as set forth in claim 18, further comprising drilling the cylindrical bores using a drill guide.

22. The method as set forth in claim 14 wherein the implantation of the plurality of reinforcement elements is done simultaneously by a part-spherically shaped tamp.

23. The method as set forth in claim 22 further comprising compacting bone graft around the end surface of the reinforcement element using the tamp.

\* \* \* \* \*